(12) United States Patent
Squilla et al.

(10) Patent No.: US 7,499,579 B2
(45) Date of Patent: Mar. 3, 2009

(54) METHOD AND PROGRAM FOR COMPARING THE SIZE OF A FEATURE IN SEQUENTIAL X-RAY IMAGES

(75) Inventors: John R. Squilla, Rochester, NY (US); John T. Boland, Fairport, NY (US); John P. Spoonhower, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 442 days.

(21) Appl. No.: 10/837,794

(22) Filed: May 3, 2004

(65) Prior Publication Data

US 2005/0244043 A1 Nov. 3, 2005

(51) Int. Cl.
*G06K 9/00* (2006.01)
(52) U.S. Cl. .................. 382/132; 378/168; 378/205; 433/72; 40/704
(58) Field of Classification Search .............. 382/132; 378/168, 205; 433/72; 40/704
See application file for complete search history.

(56) References Cited

U.S. PATENT DOCUMENTS

| | | | |
|---|---|---|---|
| 3,706,883 A | 12/1972 | McIntyre | |
| 3,848,136 A | 11/1974 | Seldin | |
| 4,394,770 A | 7/1983 | La Franca | |
| 4,941,164 A * | 7/1990 | Schuller et al. | 378/205 |
| 5,166,967 A * | 11/1992 | Fabian | 378/168 |
| 5,285,785 A | 2/1994 | Meyer | |
| 5,416,822 A * | 5/1995 | Kunik | 378/162 |
| 5,822,396 A | 10/1998 | Navab et al. | |
| 5,970,119 A | 10/1999 | Hofmann | |
| 2002/0114425 A1* | 8/2002 | Lang et al. | 378/56 |
| 2003/0044751 A1* | 3/2003 | Deslauriers et al. | 433/72 |

* cited by examiner

*Primary Examiner*—Bhavesh M Mehta
*Assistant Examiner*—Eueng-Nan Yeh

(57) ABSTRACT

A method of comparing the size of a feature in sequential X-ray images includes the steps of: forming first and second sequential X-ray images including an image of the feature, an image of a first target located directly adjacent the feature and an image of a second target located between the object and an X-ray detector; calculating scale factors for the first and second X-ray images based on the relative sizes of the images of the first and second targets in the X-ray images; measuring the sizes of the feature in the first and second X-ray images; adjusting the measured sizes of the feature in the first and second X-ray images by the respective scale factors; and comparing the adjusted measured sizes. A computer program product for performing the method is also provided.

19 Claims, 7 Drawing Sheets

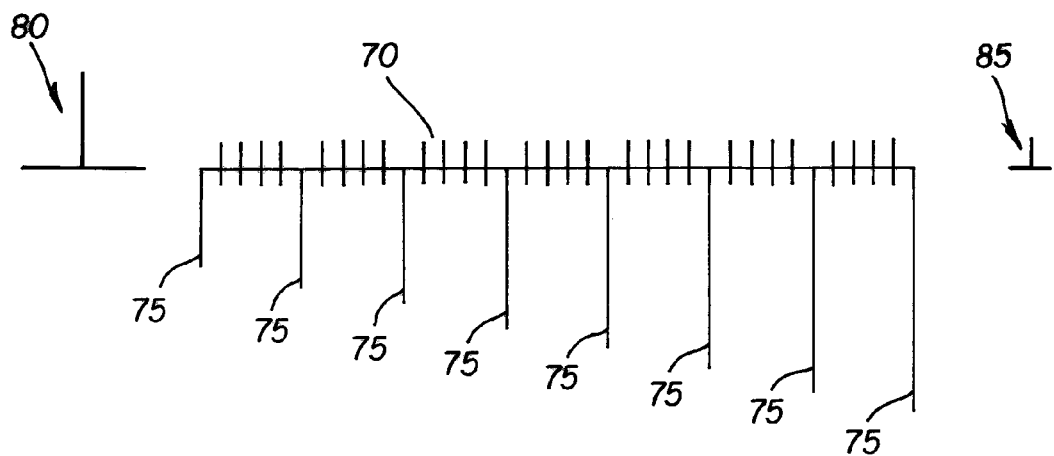
FIG. 8
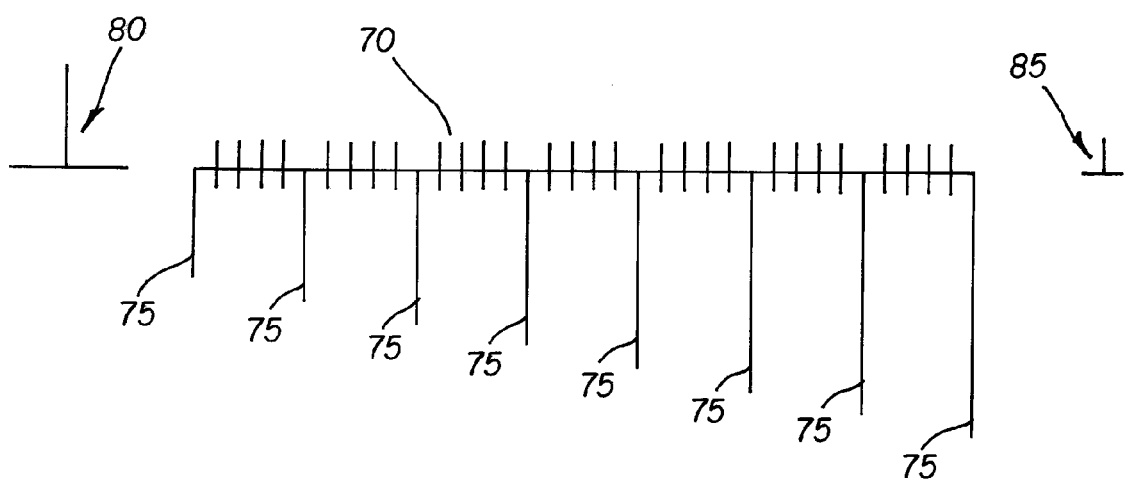

METHOD AND PROGRAM FOR COMPARING THE SIZE OF A FEATURE IN SEQUENTIAL X-RAY IMAGES

FIELD OF THE INVENTION

The invention relates generally to the field of dental imagery, and in particular to image comparison as related to dental X-ray imagery.

BACKGROUND OF THE INVENTION

Some of the more serious consequences of periodontal disease include changes in bone structure around teeth. Typically, detecting these changes in bone structure requires the comparison of sequential radiographs recorded over time for the affected areas. These comparisons may be made both visually and by using subtractive methods via computer, but both these methods suffer from the same significant shortcomings which will now be described.

Current dental radiographic equipment and procedures include the use of devices for ensuring proper set-up of the radiographic system. Such devices include beam size rulers and dental beam diameter gauges for measuring beam size; a mesh for determining focus and clarity; and comparators and pinhole cameras for measuring focal spot size. Devices used for measuring the size of features in an X-ray image include radio-opaque rulers and Fixott-Everett grids.

The Fixott-Everett grid is generally placed in contact with the X-ray film during exposure and results in a grid of known size being imaged on the film. Dental rulers are used to measure the size of a feature in an image on the X-ray film. However, these devices and methods alone provide no way to determine if the scale on the film is other than 1:1, nor do they ensure that the scale is consistent between X-rays taken at different times, and with different set-ups. Due to the divergent nature of the X-ray beam and the varying separation between the X-ray source, the tooth, and the film, measurements made directly on the film, whether with a ruler or a grid, fail to account for the attendant scale change.

Consequently, a precise determination of the size of the a feature is not possible from X-ray to X-ray due to the effects on scale caused by the problems described above. While qualitative assessments such as "bigger" or "smaller" are sometimes possible, what is required is the ability to precisely determine the relative increase or decrease in size of a feature between subsequent X-ray images, and the rate of that change.

Thus, there remains a need therefore for an improved method of determining the change in size of features which has taken place between subsequent X-ray images.

SUMMARY OF THE INVENTION

The need is met according to the present invention by providing a method and a computer program for comparing the size of a feature of an object in sequential X-ray images that includes the steps of: forming first and second sequential X-ray images including an image of the feature, an image of a first target located directly adjacent the feature and an image of a second target located between the feature and an X-ray detector, the second target having a known size relationship to the first target; calculating scale factors for the first and second X-ray images based on the relative sizes of the images of the first and second targets in the X-ray images; measuring the sizes of the feature in the first and second X-ray images; adjusting the measured sizes of the feature in the first and second X-ray images by the respective scale factors; and comparing the adjusted measured sizes.

The present invention has the advantages of allowing X-rays from different times and set-ups to be compared on an equalized scale basis. The invention accounts for divergence of an X-ray beam; the angle of the beam relative to the film surface; and for varying distance between source and film.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 8 shows a target that is useful in computer-automated comparison of features in sequential X-ray images; and FIG. 9 shows a target that is useful in computer-automated comparison of features in sequential X-ray images.

DETAILED DESCRIPTION OF THE INVENTION

Figure 1:
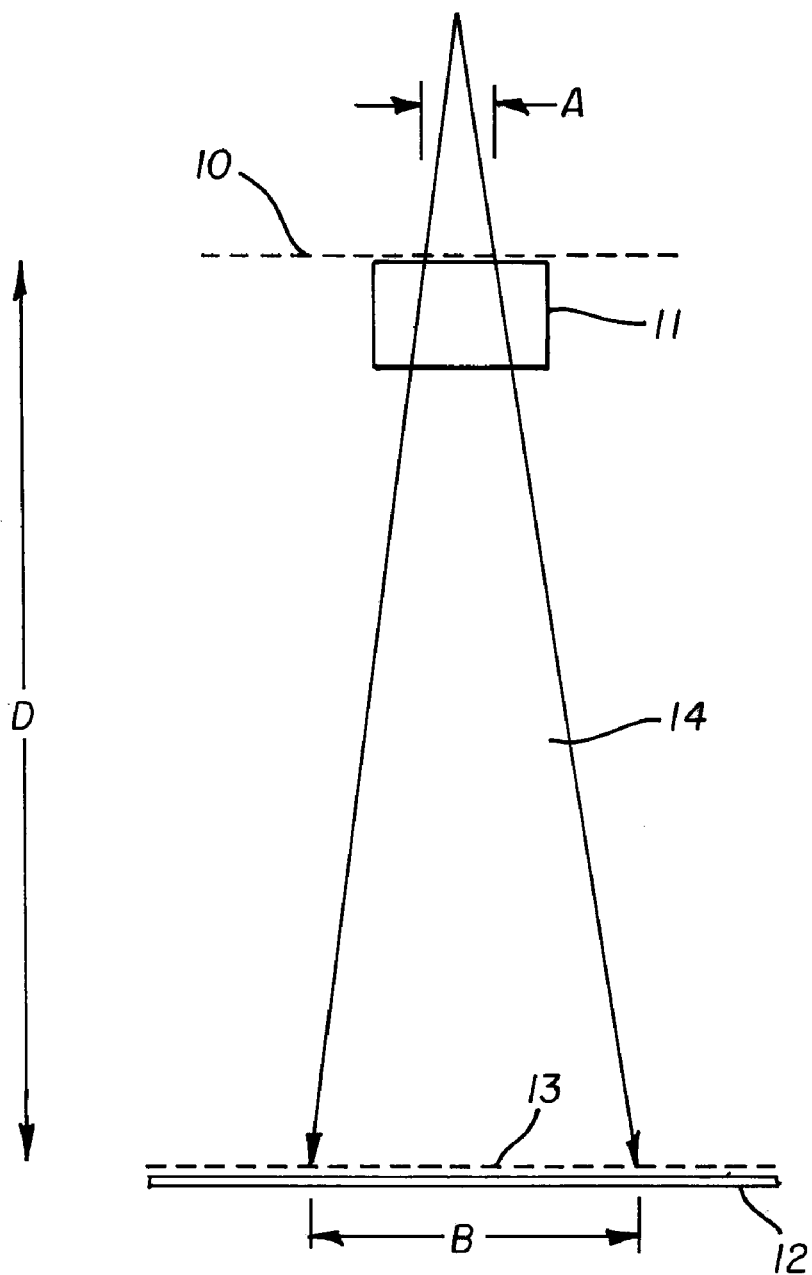
FIG. 1 is a top view of the X-ray imaging event showing the divergent X-ray beam in relation to the X-ray film, the tooth and the target.

Referring to FIG. 1, a first target 10 is placed next to a feature 11, comprising, for example, a patient's tooth and the bone area adjacent to the tooth. A projection of the feature 11 and the target 10 are both imaged on an X-ray detector, such as an X-ray film 12, placed some separation distance 13 from the first target 10. Due to the divergence of the X-ray beam 14, the size A of a scale on the first target 10 increases to size B when the beam arrives at the X-ray film 12. The X-ray image is provided with an image of a second target (not shown) having a scale which is either identical in size to that of the first target 10, or which has a size relationship to the first target 10 which is known. The second target can be located at a known position from X-ray film 12, but is preferably either located directly adjacent the film 12, or has been pre-exposed onto the X-ray film 12.

Figure 2:
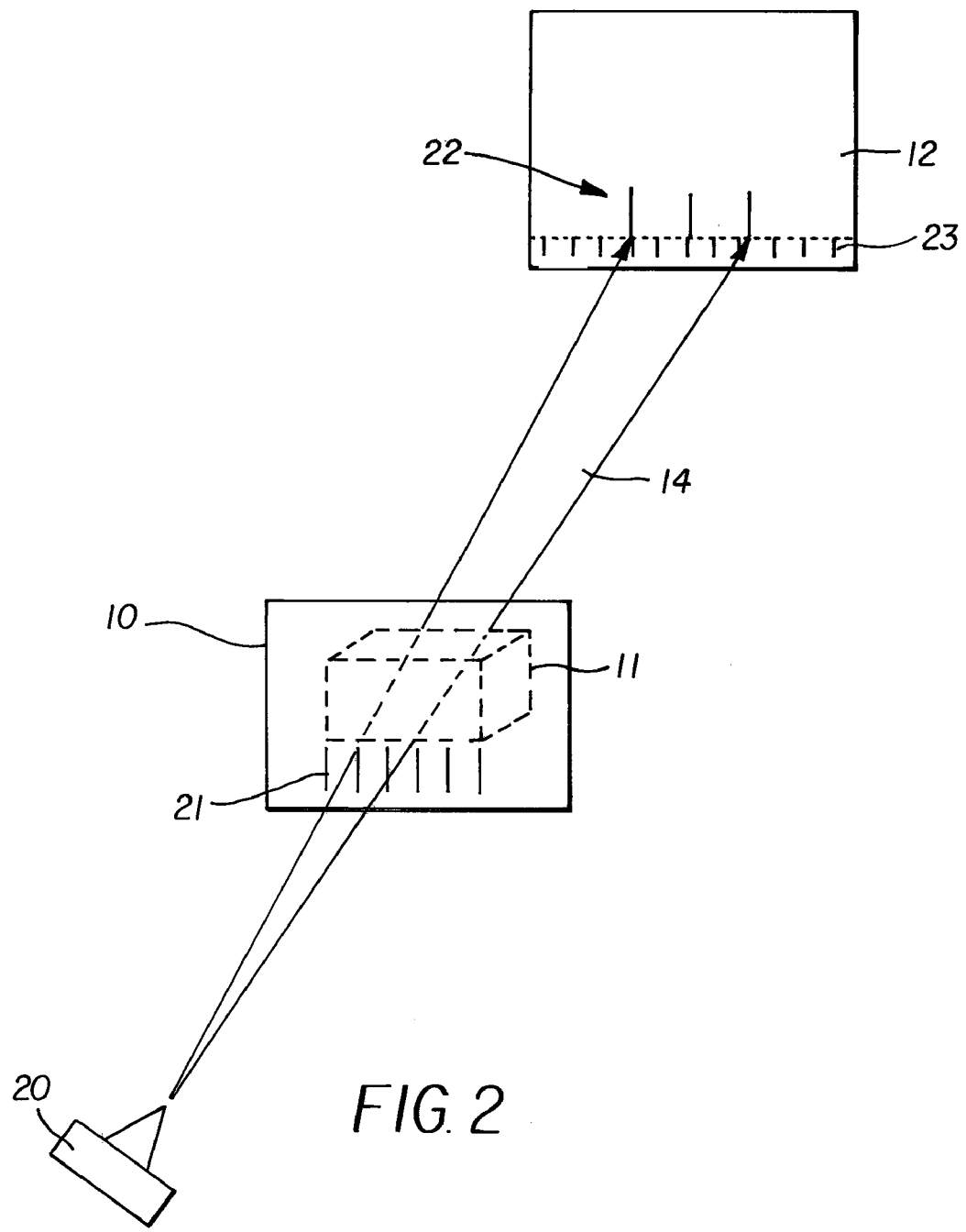
FIG. 2 is a perspective view of the same imaging event.

FIG. 2 provides a perspective view, wherein an X-ray source 20 emits a divergent X-ray beam 14 that passes through the target 10 having first target lines 21, and then the feature 11 and strikes the X-ray film 12 with pre-exposed second target lines 23. When the film is developed, the image will contain an image of the projection of the feature 11, an image of projected first target lines 22, and an image of second target lines 23. The separation of the image of the first target lines 22 can be seen to be larger than they are on the target due to the divergence of the X-ray beam 14.

Figure 3:
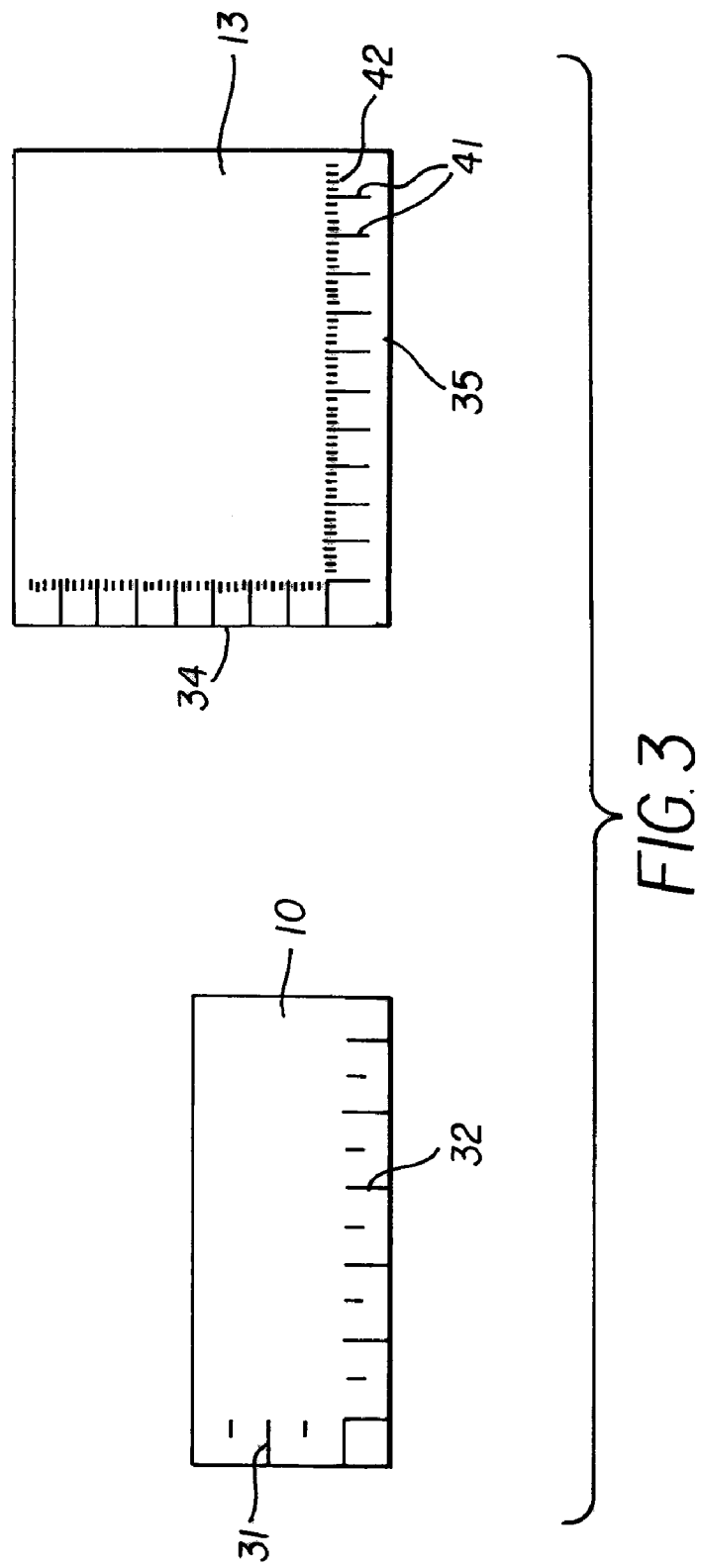
FIG. 3 is a depiction of the vertical and horizontal scale lines applied to the target and to the X-ray film.

FIG. 3 shows example configurations for an orthogonal linear first target 10 and the pre-exposed second target image 13 on X-ray film 12. Horizontal and vertical scales 31, 32 and 34, 35 are used for the first target 10 and second target 13 respectively. The second target 13 includes major second scale lines 41 and minor second scale lines 42 to aid in scale comparison as described below. The dimensions of the scales of target 10 and target 13 are either identical, or are of a known relationship one to the other. Other target configurations which may be used include: horizontal targets only, as shown in FIGS. 1 and 2; vertical targets only; a plurality of vertical and or horizontal targets; and rectangular targets.

The use of horizontal target lines 32, 35 in combination with vertical target lines 31, 34 allows a differential scale of exposure between sequential radiographs to be detected, as well as rotation between the target and the X-ray film. The use of horizontal and vertical target lines along the periphery of the image also represents a good trade-off between ease (and accuracy) of measurement and providing a suitably large unobstructed image area.

Alternatively, the targets could employ rectangular grids that extend across the image area. This arrangement would provide improved measurement while increasing the potential for obscuration.

Figure 4:
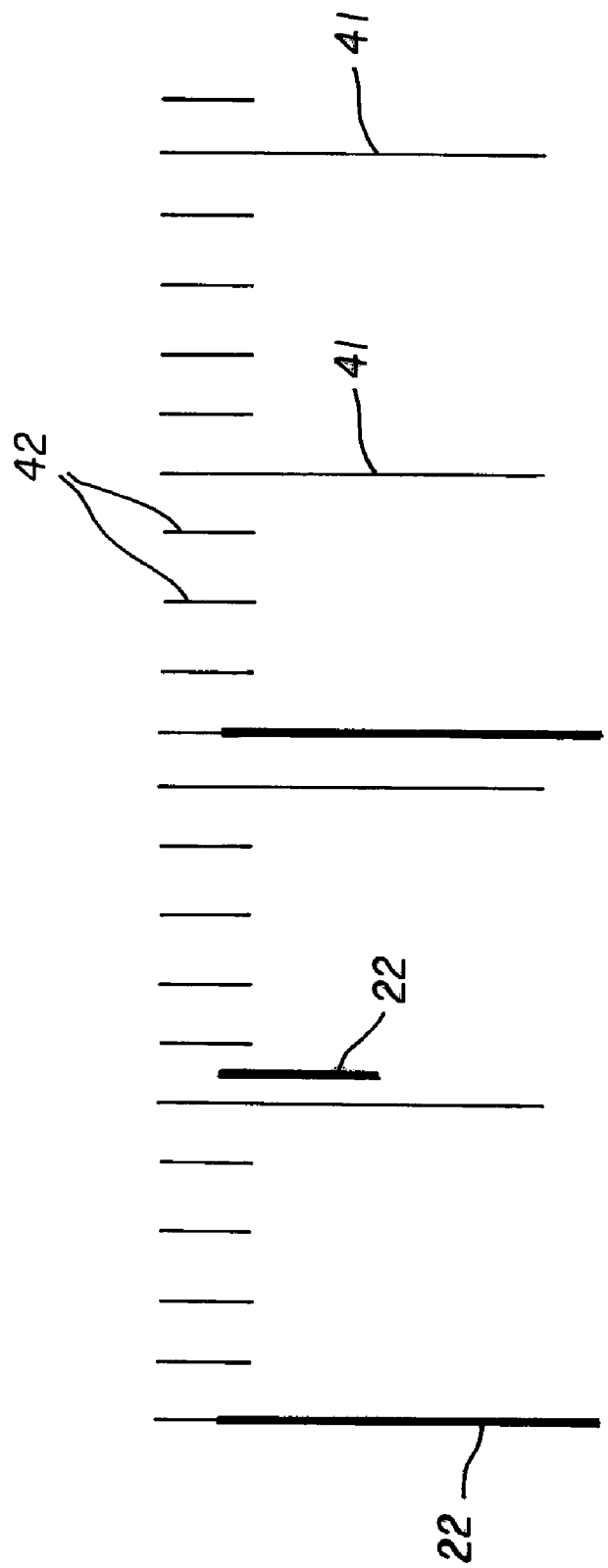
FIG. 4 is a detailed view of the target scale lines projected onto the X-ray film.

FIG. 4 shows a detail of the image of the projected first target lines 22 that can be compared to the major 41 and minor 42 second target 13 scale lines on the X-ray film. The use of the major and minor scale lines on the X-ray film allows the relative sizes of the first and second targets to be read directly. In the case illustrated in FIG. 4, comparison of the projected first target lines 22 and the major and minor second target lines 41 and 42 indicates the projected first target to be 10 percent larger than the second target. Thus, a scale factor of 1.1:1 is calculated. This result would indicate a scale increase of 10 percent for the subject x-ray image. Thus, any measurement made on the x-ray film should be reduced by 10 percent in order to determine its true size.

It will be understood that the 10% size reduction will apply only to those features in the X-ray where the feature, whose size is of interest, was directly adjacent to the first target (strictly speaking, in the same plane as the target).

Thus, when a second X-ray image is made at a later time for comparison purposes, e.g., to determine the increase or decrease in size of the projection of a feature, the target 10 must be placed directly adjacent the feature when the second X-ray is recorded. The imaged target lines would then be read on the second X-ray, as before, to determine a scale factor for the second image. The two scale factors would then be used to compare the measurement applied to the projection of the feature appearing in the two X-rays. For example, if the second X-ray image yielded a scale factor of 1.2:1, and the dimension of the feature of interest measured 12 units, this could be compared to the first X-ray image by adjusting for both scale factors (12 units×1.1/1.2=11 units). The result of 11 units can be directly compared with any measurement taken from the first X-ray image. Alternatively, each X-ray measurement can be adjusted by its individual scale factor in order to take the measurement back to true size. Using this approach, measurements can be compared at any time without reference to the scale factors of other images. In the case of an assessment of the bone in the region of a tooth in a patient with periodontal disease, an accurate assessment of any changes in shape over the time between the two X-rays, such as receding of the bone around the tooth socket, can be accurately made.

Obliquity of the x-ray beam relative to the X-ray detector can result in a differential scale factor across the surface of the detector. The use of a repeated pattern in both the first and second target allows this condition to be recognized and corrected. Obliquity would manifest itself as a difference in apparent scale difference across the scales, with the difference being less at the end of the scale closest to the X-ray source.

The first and second targets can also be designed to enhance detection and measurement using computer algorithms (automated measurement). An example of a target design useful for automated detection is illustrated in FIGS. 8 and 9. As illustrated, an upper target scale 70 is shown with a repeating indicium inserted in the scale periodically. As further illustrated, a lower target scale 75 is shown with different repeating indicia of increasing lengths. Digital image data files are then generated from an X-ray in which upper and lower target scales 70 and 75 appear, either by electronic scanning of the processed X-ray film, or by direct digital capture of the original X-ray exposures. Using known prior art computer pattern recognition techniques, the two different scales 70 and 75 may be automatically recognized by a computer. The difference in the dimensions of the repeating scale line patterns for the two scales may then be determined automatically, again using known pattern recognition techniques. Once the dimensions of the two scales are determined, then the scale factor for the X-ray in question may be readily calculated automatically by a simple computer algorithm. As illustrated in FIG. 9, a larger left sample target scale 80 and a smaller right sample target scale 85 include orthogonal scales arranged to be exposed on opposite sides of the upper target scale 70.

In an alternative embodiment, the digital image of the X-ray is displayed on an electronic display screen (not shown). Using a suitable user interface, the user simply identifies the two scales by pointing to them using a mouse or other user input device. Once the scales have been so marked, simple computer algorithms, made in accord with known prior art techniques, automatically makes measurements, and computes scale and differential scale in vertical and horizontal directions.

Figure 5:
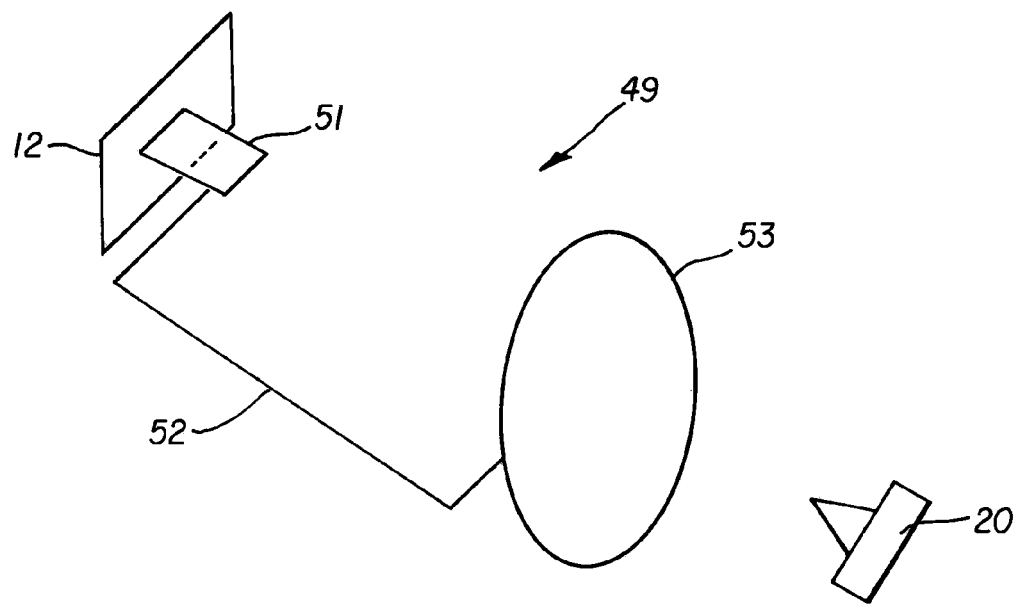
FIG. 5 is a depiction of a prior art intraoral film positioner with bite plate and aiming ring.

FIG. 5 shows a prior art intraoral film positioner designated 49 with an integral X-ray aiming ring 53. In typical use, the X-ray film 12 is mounted on a bite plate 51 to locate the X-ray film 12 placed on the lingual side of the patient's teeth when the patient bites down on the bite plate 51. A rod 52 connected to the bite plate 51 positions the X-ray aiming ring 53 outside of the patient's mouth and an operator aims the X-ray source 20 through the aiming ring 53 at the X-ray film 12. Note that the aiming ring 53 does not precisely control distance or angle of the X-ray source 20 relative to the X-ray film 12.

Figure 6:
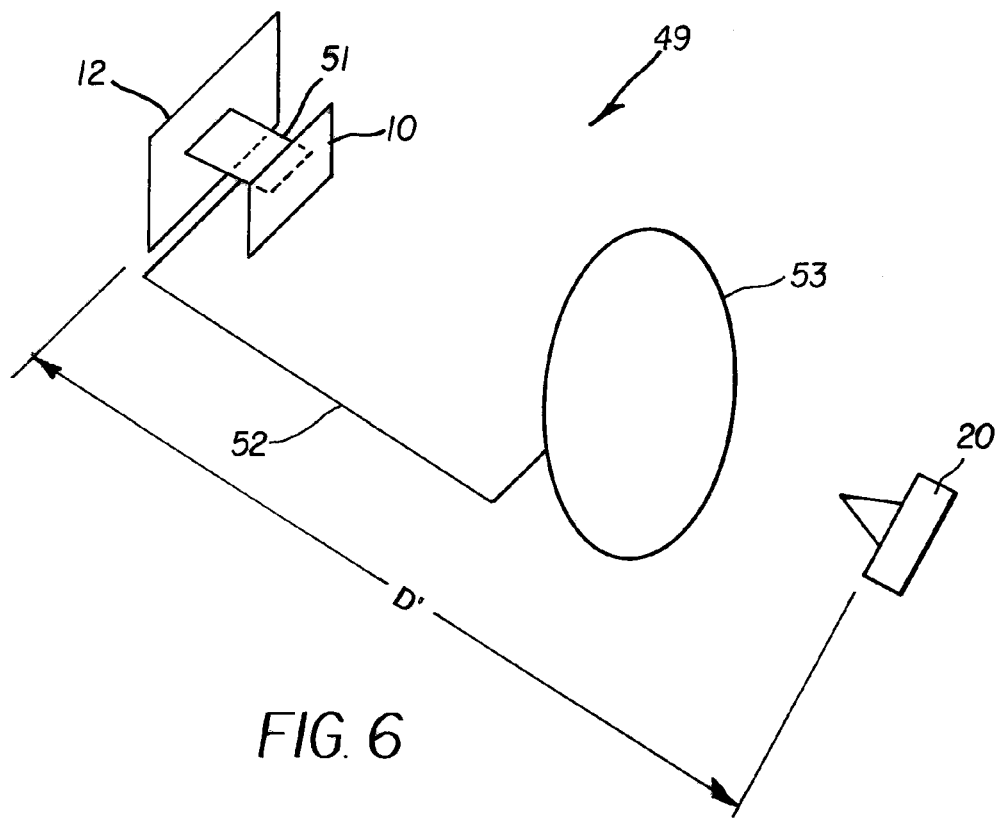
FIG. 6 is a depiction of an intraoral film positioner with bite plate, aiming ring and the addition of the scale target.

Referring to FIG. 6 a first target 10 is mounted for movement along the other end of bite plate 51 of the intraoral positioner 49. The first target 10 could be a permanent part of the intraoral positioner 49, or it could be removable and disposable. Mounting surfaces (not shown) maintain the parallel alignment of X-ray film 12 and first target 10. The mounting surfaces are located on the bite plate 51 so that the patient's tooth or teeth (not shown) fall between the first target 10 and the X-ray film 12. The X-ray film 12 is positioned on the lingual side of the tooth, and the first target 10 on the buccal side of the patient's tooth. The first target 10 is moved towards the tooth and effectively cinches the tooth between the first target 10 and the X-ray film 12. At this point the target is positioned between the X-ray source 20 and the X-ray film 12, with the tooth cinched in between the target 10 and X-ray film 12. The resultant image of the first target 10 and the second target 13 that was pre-exposed on the film is used to compute the scale factor for the exposure exactly as described earlier for the example of FIG. 4. When subsequent X-rays are recorded of the same tooth, any differences in scale resulting from differences in the distance between the X-ray source 20 and the target 10 in these subsequent X-rays may be corrected for by computing the scale of the subsequent exposures, again as described previously for the example of FIG. 4. It will be recognized that the critical factors in the successful use of the present invention are first, that the target 10 always be placed directly against the tooth or other feature, and second, that the film 12 and target 10 be held in parallel alignment. In this way, a scale factor for the projection of the feature onto the film 12 can be accurately computed, regardless of the position of the X-ray source, or even in the position of the film 12. In certain situations, because of the size of the film, or the position in the mouth, it may be impossible to position the film 12 against the lingual side of a tooth or other feature, but as long as the film 12 is held against the buccal side of the feature, and the target 10 and film 12 are held parallel, then a scale factor for the projection can be calculated.

Figure 7:
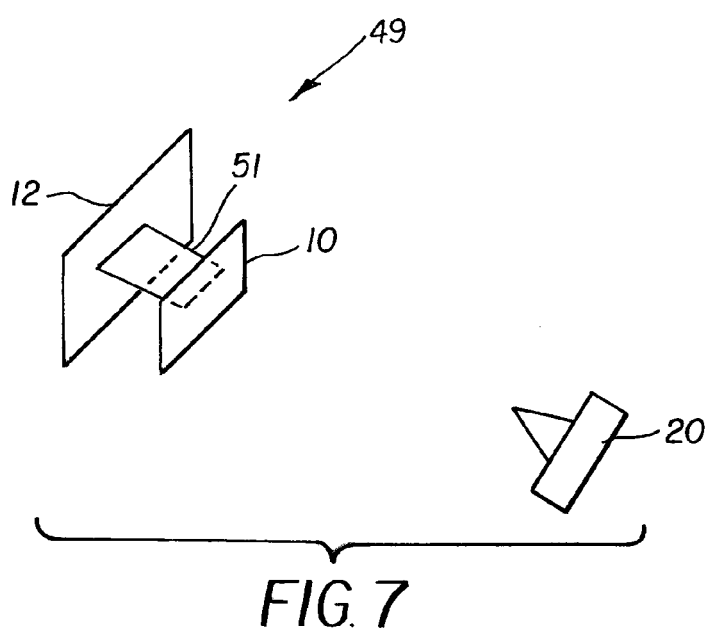
FIG. 7 is a depiction of an intraoral film positioner with bite plate, without an aiming ring.

FIG. 7 shows an intraoral film positioner without an aiming ring. In this case the X-ray film 12 with a pre-exposed second target 13 (not visible) is placed next to the lingual side of the feature. As the patient bites down on the plate 51, the first target 10 is positioned in between the X-ray film 12 and the X-ray source 20. This configuration provides less control over the angle of exposure by the X-ray source 20, but as described previously for the example of FIG. 4, the image of the projected target 10 allows for recognition and correction for any obliquity in the exposure.

In the preceding description, an embodiment of the present invention has been described as a method of comparing the size of a feature in sequential X-ray images. However, in another embodiment, the present invention comprises a computer program product for comparing the size of a feature in sequential X-ray images. In describing the present invention, it should be apparent that the computer program of the present invention can be utilized by any well-known computer system. However, many other types of computer systems can be used to execute the computer program of the present invention. Consequently, the computer system will not be discussed in further detail herein.

The computer program for performing the method of the present invention may be stored in a computer readable storage medium. This medium may comprise, for example; magnetic storage media such as a magnetic disk (such as a hard drive or a floppy disk) or magnetic tape; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

The invention has been described in detail with particular reference to certain preferred embodiments thereof, but it will be understood that variations and modifications can be effected within the spirit and scope of the invention.

PARTS LIST

10 target
11 tooth
12 X-ray film
13 second target
14 X-ray beam
20 X-ray source
21 first target lines
22 projected first target lines
23 second target lines
31 vertical first target scale
32 horizontal first target scale
34 vertical second target scale
35 horizontal second target scale
41 major second scale lines
42 minor second scale lines
49 intraoral film positioner
51 bite plate
52 rod
53 X-ray aiming ring
70 upper target scale
75 lower target scale
80 left sample target scale
85 right sample target scale A size of target 10 to be projected B size of target 10 as projected D separation distance between target 10 and film 12 D' separation distance between source 20 and film 12

The invention claimed is:

1. A method of comparing a dimension of a feature using sequential X-ray images, comprising steps of:
   providing an X-ray source;
   locating a first target adjacent the feature between the source and the feature;
   providing an X-ray detector on an opposite side of the feature from the source and the first target;
   locating a second target between the feature and the detector, the second target having a known size relationship to the first target;
   forming a first X-ray image of the feature, the first image including an image of both the first target and the second target;
   at a later time, locating the first target adjacent the feature and the second target between the feature and the detector;
   at the later time, forming a second X-ray image of the feature, the second image including an image of both the first target and the second target;
   calculating a first scale factor for the first X-ray image based on the relative sizes of the images of the first and second targets in the first X-ray image;
   calculating a second scale factor for the second X-ray image based on the relative sizes of the images of the first and second targets in the second X-ray image;
   measuring a dimension of the feature in the first and second X-ray images;
   adjusting the measured dimension of the feature in the first and second X-ray images by the respective first and second scale factors; and
   comparing the adjusted measured dimensions.

2. The method claimed in claim 1, wherein the second target is located on the X-ray detector.

3. The method claimed in claim 1, wherein the X-ray detector is X-ray film, and the second target is pre-exposed on the X-ray film.

4. The method claimed in claim 1, wherein the feature is a tooth, the first target and dental X-ray film are spaced and disposed substantially parallel to each other, and the first target is located on one end of a bite plate of an intraoral dental X-ray film positioner, and a dental X-ray film is located on an opposite end of the bite plate.

5. The method claimed in claim 4, wherein the second target is pre-exposed on the dental X-ray film.

6. The method claimed in claim 1, wherein the first and second targets comprise linear marks.

7. The method claimed in claim 1, wherein the first and second targets comprise rectangular grids.

8. The method claimed in claim 1, wherein the first and second targets comprise orthogonal linear scales.

9. The method claimed in claim 8, wherein the orthogonal scales of the first and second targets are arranged on opposite sides of a target scale.

10. The method of claim 1, wherein calculating scale factors comprises determining a differential scale factor across a surface of the X-ray detector.

11. A computer program product for comparing a dimension of a feature in sequential X-ray images, said images being made using an X-ray source, a first target located directly adjacent the feature between the source and the feature; an X-ray detector on an opposite side of the feature from the source and the first target; and a second target located between the feature and the detector, the second target having a known size relationship to the first target, the program product comprising:

a computer readable storage medium; and a computer program stored on the medium for performing steps of:

forming a first X-ray image of the feature, the first image including an image of both the first target and the second target;

at the later time, forming a second X-ray image of the feature, the second image also including an image of both the first target and the second target;

calculating a first scale factor for the first X-ray image based on the relative sizes of the images of the first and second targets in the first X-ray image;

calculating a second scale factor for the second X-ray image based on the relative sizes of the images of the first and second targets in the second X-ray image;

measuring a dimension of the feature in the first and second X-ray images;

adjusting the measured dimension of the feature in the first and second X-ray images by the respective first and second scale factors; and comparing the adjusted measured dimensions.

12. The computer program product of claim 11, wherein the second target is located on the X-ray detector.

13. The computer program product of claim 11, wherein the X-ray detector is X-ray film, and the second target is pre-exposed on the X-ray film.

14. The computer program product of claim 11, wherein the feature is a tooth, the first target and dental X-ray film are spaced and disposed substantially parallel to each other, and the first target is located on one end of a bite plate of an intraoral dental X-ray film positioner, and a dental X-ray film is located on an opposite end of the bite plate.

15. The computer program product of claim 14, wherein the second target is pre-exposed on the dental X-ray film.

16. The computer program product of claim 11, wherein the first and second targets comprise linear marks.

17. The computer program product of claim 11, wherein the first and second targets comprise rectangular grids.

18. The computer program product of claim 11, wherein the first and second targets comprise orthogonal linear scales.

19. The computer program product of claim 18, wherein the orthogonal linear scales of the first and second targets are arranged on opposite sides of a target scale.

* * * * *